United States Patent [19]

Jelly

[11] Plant 4,173

[45] Dec. 27, 1977

[54] ROSE PLANT-CHARISMA VARIETY

[75] Inventor: Robert G. Jelly, Richmond, Ind.

[73] Assignee: The Conard-Pyle Company, West Grove, Pa.

[21] Appl. No.: 760,412

[22] Filed: Jan. 18, 1977

[51] Int. Cl.[2] ..... A01H 5/00

[52] U.S. Cl. ..... Plt./22

[58] Field of Search ..... Plt./22

*Primary Examiner*—Robert E. Bagwill

*Attorney, Agent, or Firm*—Burns, Doane, Swecker & Mathis

[57] ABSTRACT

A rose plant of the Floribunda class originated by crossing Gemini (U.S. Plant Pat. No. 2,728) with Zorina (U.S. Plant Pat. No. 2,321).

1 Drawing Figure

SUMMARY OF THE INVENTION

My invention relates to a new and distinct variety of rose plant of the Floribunda class originated by me in 1968 as a result of a breeding program using Gemini (U.S. Plant Pat. No. 2,728) as pollen parent and Zorina (U.S. Plant Pat. No. 2,321) as seed parent.

The objective of this breeding program was to combine the strong vivid coloring of both parents, along with the superb blooming qualities and the superb dark green foliage. I was successful in achieving this objective. As a result of this crossing, I have produced a new and useful rose variety which is distinguished from its parents, and all rose varieties of which I am aware, as evidenced by the following unique combination of characteristics:

1. A plant of compact and freely branched growth.
2. A plant habit of even regular form having a neat well balanced appearance, with very attractive distinctive foliage.
3. A floriferous plant producing good quantities of flowers in clusters on the stem.
4. Flowers of substantially uniform size.
5. Flowers having a distinctive combination of flame red and yellow colors.

Asexual reproduction of my new variety by budding as performed at Richmond, Ind. and West Grove, Pa. shows that all characteristics of the variety are established and transmitted through succeeding propagations.

BRIEF DESCRIPTION OF THE DRAWING

The accompanying drawing shows typical specimens of the vegetative growth and flowers of my new variety in different stages of development as depicted in color as nearly true as is reasonably possible to make the same in a color illustration of this character.

DETAILED DESCRIPTION OF THE DISCLOSURE

The following is a detailed description of my new variety with color terminology in accordance with the Royal Horticultural Society Colour Chart of the Royal Horticultural Society, London, England.

Type: Hardy, bush, outdoor; for garden decoration.
Class: Floribunda
Progpagation: It does hold its distinguishing characteristics through succeeding propagations by budding.

FLOWER

Locality where grown: West Grove, Pa.
Flowers borne: Several to stem; in rounded cluster; on short stems.
Quantity of bloom: Abundant, outdoors.
Continuity: Continuous.
Fragrance: Slight; centifolia.
Bud: Peduncle: Medium length; medium thickness; erect; light green; 142 A at the connection to the hip; medium; few hairs; numerous prickles; red.

*Before calyx break.*—Size: Small. Form: short ovoid with a conspicuous neck; with foliaceous appendages on the surface of the bud; with slender bristle like foliaceous parts extending beyond the tip of the bud equal to ¼ of its length.

*As calyx breaks.*—Color: 46A on the exposed portion of the petal.

*As first petal opens.*—Size: Small. Form: Ovoid. Color: Outside: 150C at the point of attachment changing to 46A where the petal was exposed to the sun. Inside: 145C at the point of attachment and 184C at the petal margin. Opening: It does open up well.

Bloom: Size when fully open: Small, 4.4 cm. to 5 cm.

*Petalage.*—Double (more petals, but the stamens not hidden); from 35 to 45 petals; arranged regularly.

*Form.*—High-centered at first; becoming globular; petals remaining at first tightly rolled outward; becoming later at maturity tightly rolled outward.

Petals: Medium soft; with inside shiny; outside satiny.

*Shape.*—Outer: Mostly round; scalloped; with 1 notch. Intermediate: Ovate; scalloped; with 1 tooth. Inner: Ovate; scalloped; with 1 notch.

*Color.*—Colors may be modified by being washed with other colors.

This description of a newly opened flower was made from a rose grown outdoors in July, 1975 at West Grove, Pa. 19390.

*Color.*—Outer petal: Outside surface — 12A at the point of attachment, approximately two thirds of the way up the petal blending to 30C, darkening to 33A at the petal margin. Inside surface — 146D at the point of attachment, becoming 13C two thirds of the way up the petal, becoming 33B and finally 33A at the petal margin. Intermediate petal: Outside surface — 12 A at the point of attachment, becoming 12B ¾ the way up the petal, becoming 32C and 32B at the petal margin. Inside surface — 12A at the point of attachment, becoming 33B two thirds of the way up the petal and 33B at the petal margin. Inner petal: Outside surface— 12A at the point of attachment, becoming 33C two thirds of the way up the petal, darkening to 33A at the petal margin. Inside surface — 12A at the point of attachment, becoming 33C half the way up the petal, and darkening to 33B at the petal margin.

This description was made from a rose that was open for three days, outdoors in July, 1975 at West Grove, Pa. 19390.

*Color.*—Outer petal: Outside surface — At the point of attachment 7A, 30C at the center of the petal, becoming 33A at the petal margin. Inside surface — 2B at the point attachment, becoming 12A at the center of the petal becoming 33A at the petal margin. Inner petal: Outside surface — 12A at the point of attachment, becoming 32B, and darkening to 32A at the petal margin. Inside surface — 9A at the point of attachment, becoming 9B half way up the petal, becoming 32A at the petal margin.

*General color effect.*—Newly opened flower: 33A on the outer petals, blending with yellow to 13C at the center of the bloom. Three days open: 33A at the outer petals blending to 12A at the center of the bloom.

*Behavior.*—Persist; fading purple.

*Flower longevity.*—On bush in garden 10–12 days in July; grown outdoors kept at living room temperatures 12–15 days in July.

Reproductive organs:

*Stamens.*—Medium number; arranged regularly about pistils.

*Filaments.*—Many; with anthers; medium length. Color: 9A

*Anthers.*—All open at once; small size. Color: 5D. Seldom an anther fused with a petaloid.

*Pollen.*—Very sparse. Color: orange 28B.

*Pistils.*—Many.

*Styles.*—Uneven; long length; medium; bunched.

*Stigma.*—Yellow.

*Ovaries.*—All enclosed in receptacle.

*Hips.*—Short, ovoid; pear shaped; hairy; walls medium; green-gray.

*Sepals.*—Permanent; medium length; recurved.

*Seeds.*—Medium number; small size.

PLANT

Foliage: Leaves: compound of 7 leaflets; abundant; medium size; leathery, glossy.

*Leaflets.*—Shape: Ovoid with apex acute, base obtuse, margin serrate.

*Color.*—Mature — Upper surface: 137A with 187A at the leaf margins. Under surface: 139C. Young — Upper surface: 144A becoming 187A at the margin. Under surface: 139C becoming 187B at the margin.

*Rachis.*—Medium — Upper side: Grooved, prickly. Under side: Moderately prickly.

*Stipules.*—Medium; narrow; medium points; turning out at an angle of 45°; recurved toward the stem.

*Disease.*—Resistant to mildew and blackspot. Resistance comparable to the average variety growing under the same cultural conditions.

Growth:

*Habit.*—Bushy, much branched.

*Growth.*—Vigorous.

*Canes.*—Medium.

*Main stems.*—Dull. Color: 146B.

*Prickles.*—Several. Color: 177B

*Hairs.*—None.

*Branches.*—Color 144B.

*Prickles.*—Color 175A.

*Hairs.*—None.

*New shoots.*—Color: 83A.

*Prickles.*—Few; Color: 185A.

*Hairs.*—None.

Hardiness: Withstands moderate sub-zero temperatures.

I claim:

1. A new and distinct variety of rose plant of the Floribunda class substantially as herein shown and described, characterized particularly as to novelty by a unique combination of vibrant multicolor bloom, vigorous habit of growth, excellent foliage having resistance to mildew and blackspot, ability to withstand moderate sub-zero temperatures, and an ability for its cut flowers to last 12 to 15 days at room temperature indoors.

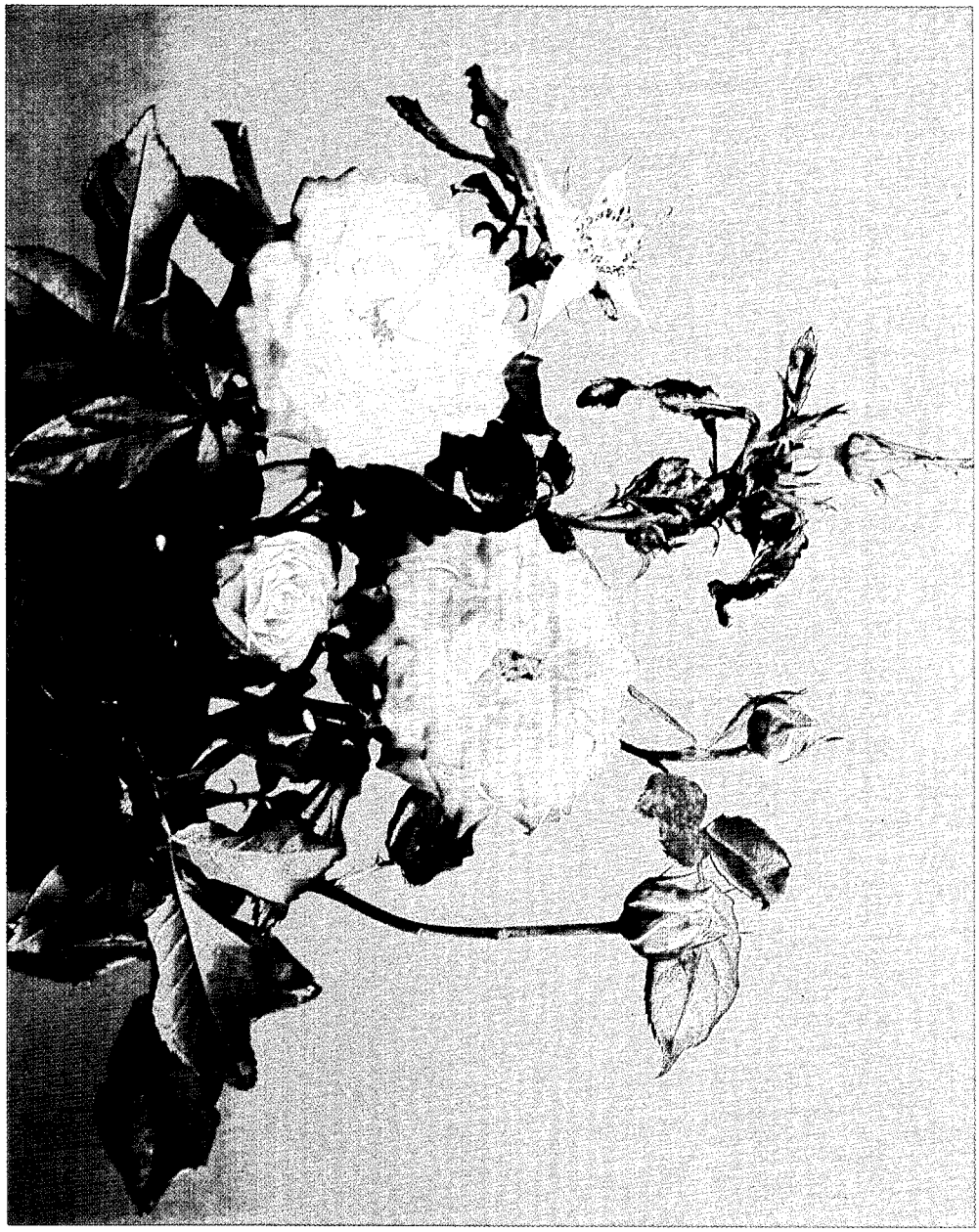

* * * * *